United States Patent [19]

Schiehser et al.

[11] Patent Number: 4,788,306
[45] Date of Patent: Nov. 29, 1988

[54] FLUOROOXIRANE CARBOXYLATES AS HYPOGLYCEMIC AGENTS

[75] Inventors: Guy A. Schiehser, Malvern; Donald P. Strike, St. Davids, both of Pa.

[73] Assignee: American Home Products Corporation, New York, N.Y.

[21] Appl. No.: 88,189

[22] Filed: Aug. 21, 1987

Related U.S. Application Data

[63] Continuation-in-part of Ser. No. 34,528, Apr. 3, 1987, abandoned, which is a continuation-in-part of Ser. No. 26,339, Mar. 16, 1987, abandoned.

[51] Int. Cl.<sup>4</sup> .......................................... C07D 303/48
[52] U.S. Cl. .................................... 549/549; 514/884
[58] Field of Search ........................................ 549/549

*Primary Examiner*—Norma S. Milestone
*Attorney, Agent, or Firm*—George Tarnowski

[57] ABSTRACT

There are disclosed compounds of the formula

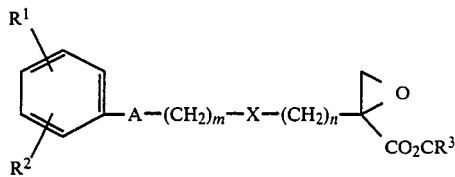

wherein
$R^1$ and $R^2$ are each, independently, hydrogen, hydroxy, lower alkyl, lower alkoxy, haloloweralkyl, haloloweralkyl sulfonyl, halo or nitro;
$R^3$ is hydrogen, lower alkyl, or aryl of 7–12 carbon atoms;

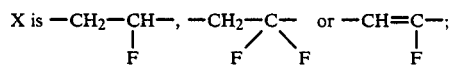

A is $-CH_2-$, $-O-$ or $-S-$;
m is 1–8;
n is 0–7, with the proviso that $m+n \leq 8$;
or a pharmacologically acceptable salt thereof, and their use as fatty acid oxidation inhibitors possessing a significantly reduced potential for impairment of normal cardiac function, and having particular utility in the treatment of glucose and fatty acid metabolism disorders, such as diabetes.

11 Claims, No Drawings

FLUOROOXIRANE CARBOXYLATES AS HYPOGLYCEMIC AGENTS

This application is a continuation-in-part of U.S. Ser. No. 34,528, filed Apr. 3, 1987, which is a continuation-in-part of U.S. Ser. No. 26,339, filed Mar. 16, 1987, now abandoned.

This invention relates to phenyl mono- and di-fluoroalkyl- and phenoxy mono- and di-fluoroalkyl-substituted oxirane carboxylic acids and their use as fatty acid oxidation inhibitors and hypoglycemic agents.

Phenoxymethyloxiranes and phenyloxiranecarboxylic acid esters have been investigated as potential substrates or inhibitors for epoxide hydrase from guinea pig liver microsomes [F. Oesch et al., Biochem., 10(26) 1971, 4858–66]. Further, 2-phenylalkyl and 2-phenoxyalkyl-substituted oxirane carboxylic acids such as those disclosed in U.S. Pat. Nos. 4,324,796 and 4,337,267, have been found to possess hypoglycemic and hypoketonemic activity, which makes them useful for the prophylaxis and treatment of disorders such as diabetes, which are based on glucose or fat metabolism.

One of the approaches to dealing with individuals having elevated blood glucose levels, such as diabetics, is the use of fatty acid oxidation inhibitors as hypoglycemic agents. The basis for this treatment approach is the recognized reciprocal relationship that exists between fat and carbohydrate metabolism. Thus, in certain individuals, such as diabetics, who often have an increased utilization of fatty aices (and also increased hepatic gluconeogenesis), a reduction in fatty acid oxidation should enhance carbohydrate utilization, with a consequent lowering of blood glucose levels. Moreover, at least as important is the fact that a decrease in hepatic fatty acid oxidation also leads to a decrease in hepatic glucose production, thereby even further reducing blood glucose levels.

The key biological mechanism by which fatty acids are oxidized resides in the rate limiting step of the transport of long chain fatty acid acyl groups into the cellular mitochondria. The long chain fatty acids are transported into the mitochondria via a carnitine dependent process catalyzed by the two enzymes, carnitine palmitoyl transferase I and II (CPT I and II). Fatty acyl CoA's are transesterified to carnitine by the enzyme CPT I on the outer aspect of the inner mitochondrial membrane. Following translocation across the mitochondrial membrane, the reverse reaction is catalyzed by CPT II. Fatty acid oxidation occurs once the fatty acids are in the mitochondria. The fatty acid oxidation inhibitors operate by inhibiting carnitine palmitoyl transferase I (CPT I), thus preventing the transport of the fatty acids into the mitochondria. The mitochondria of tissues from the liver, heart and diaphragm are highly sensitive to the effects of the fatty acid oxidation inhibitors.

The liver is an ambivalent organ with regard to preference for fatty acids or glucose for its energy source. Thus, by shutting off its supply fo fatty acids via the fatty acid oxidation inhibitors, the liver will not only consume glucose, but also decrease its glucose output, thus lowering the blood glucose levels. On the other hand, the heart derives the majority of its energy from the oxidation of fatty acids. Accordingly, a major concern about the chronic use of fatty acid oxidation inhibitors relates to their potential for cardiotoxicity or at least impairment of normal cardiac function. This potential becomes even more troublesome when one considers that the prime target patient population for the fatty acid oxidation inhibitors are diabetics, in whom the disease process is characterized by, inter alia, large vessel disease and microvascular disease, i.e., patients in whom impairment of normal cardiac function can be the least tolerated during the treatment of the underlying disease process.

The precise mechanism by which the heart transports long chain fatty acids for its utilization has not been elucidated and so it is possible that isoenzymes of CPT may be involved. In any event, it has been found that the prior art fatty acid oxidation inhibiting phenylalkylene- and phenoxyalkyl-substituted oxirane carboxylic acids demonstrate a very significant inhibition of fatty acid oxidation by cardiac tissue. See Seitelberger et al., J. Cardiovas. Pharmacol., 6 (1984) 902 and Seitelberger et al., J. Cardiovas. Pharmacol., 7 (1985) 273. The adverse cardiac effects from the chronic administration of another fatty acid oxidation inhibitor, methyl ester of 2-tetradecylglycidate, have been studied and reported by Bachmann et al., Biochem. Pharmacol., 33 (1984) 1947; Lee et al., Diabetes, 31 (1982) 12; and Lee et al., Biochem. Med., 33, (1985) 104.

It is apparent, therefor, that the ideal fatty acid oxidation inhibitor is one which exhibits a significant effect on the hepatic utilization of fatty acids and decreases hepatic glucose output, thereby resulting in preferential hepatic utilization of glucose with a concomitant lowering of blood glucose levels, while at the same time having comparatively little or no significant effect on cardiac fatty acid utilization levels. It has now been found that the novel compounds of the present invention exhibit precisely this profile of activity. The present invention provides novel compounds having the following formula:

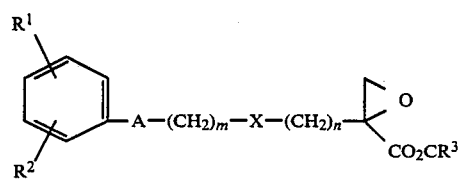

wherein $R^1$ and $R^2$ are each, independently, hydrogen, hydroxy, lower alkyl, lower alkoxy, haloloweralkyl, haloloweralkyl sulfonyl, halo or nitro;

$R^3$ is hydrogen, lower alkyl, or aryl of 7–12 carbon atoms;

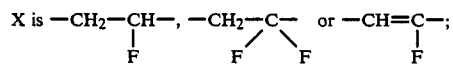

A is $-CH_2-$, $-O-$ or $-S-$;

m is 1–8;

n is 0–7, with the proviso that $m+n \leq 8$;

or a pharmacologically acceptable salt thereof.

The terms "lower alkyl" and "lower alkoxy" refer to moieties having 1 to 6 carbon atoms in the carbon chain. The term "halo" refers to fluoro, bromo or chloro.

The pharmacologically acceptable salts include those of pharmacologically acceptable inorganic and organic acids, such as hydrochloric, hydrobromic, sulfuric, nitric, phosphoric, methanesulfonic, benzenesulfonic, acetic, citric, fumaric, malic, maleic, succinic and the like. Cations used for salt formation are those of the alkali metals, alkaline earth metals or earth metals, such as lithium, sodium, potassium, magnesium, calcium and aluminum. Cations corresponding to organic nitrogen bases, such as amines, aminoalkanols, aminosugars and basic amino acids may also be used. Examplary of the latter are ethylenediamine, dimethylamine, diethylamine, morpholine, piperidine, piperazine, methylcyclohexylamine, benzylamine, ethanolamine, di- and triethanolamine, tris-(hydroxymethyl)aminomethane, glucamine, glucosamine, lysine, ornithine, arginine and the like.

The compounds of the invention by virtue of their configuration, exhibit stereoisomerism. Accordingly, the compounds of the invention include the diasteriomers, enantiomorphs, racemates and mixtures thereof.

The compounds of the invention can be prepared by a variety of synthetic routes using conventional methods. According to one preparative scheme, for example, a suitable aldehyde is first reacted with methyl acrylate to given an allylic alcohol intermediate:

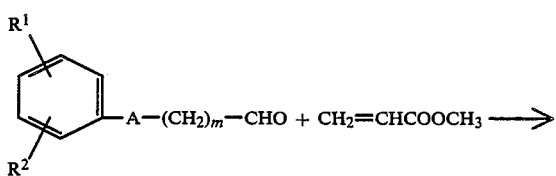

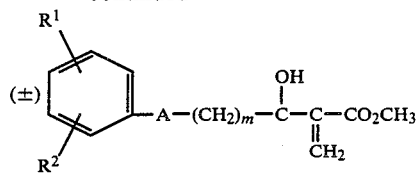

-continued

The allylic alcohol intermediate is then fluorinated to afford the allylic fluoride, which is then subjected to epoxidation to yield a mixture of two diastereomeric fluoroepoxides, which can be resolved by chromatographic separation:

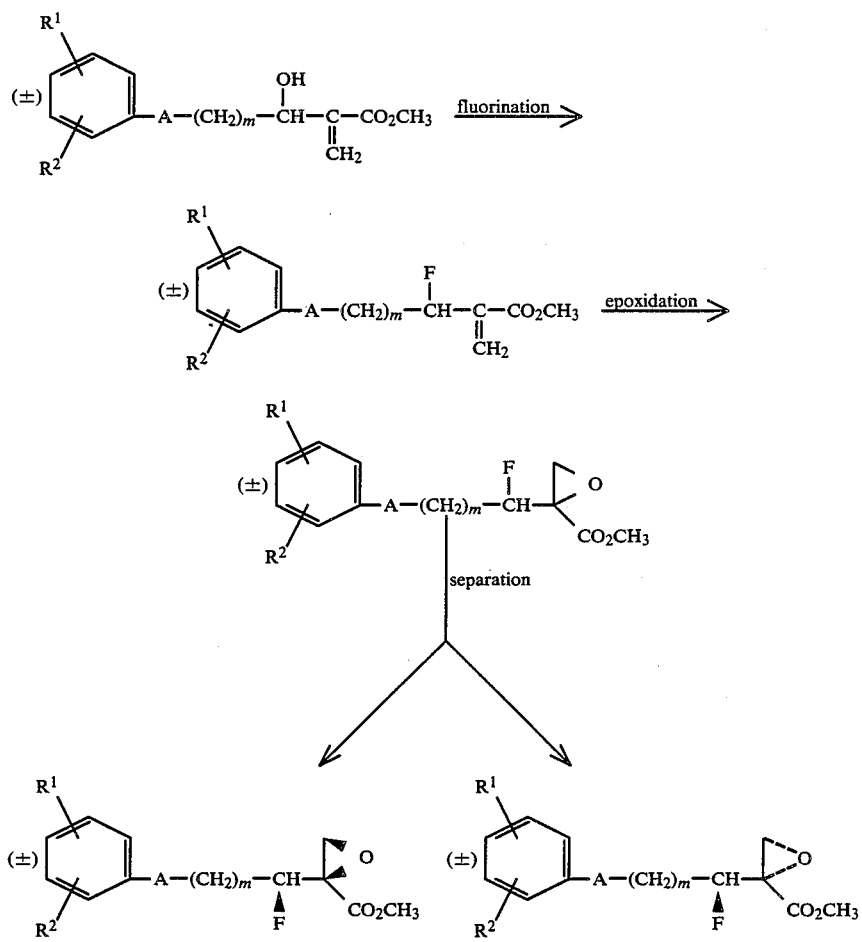

In an alternative scheme, the allylic alcohol may be first epoxidized to yield two diastereomeric epoxyalcohols. This mixture can then be fluorinated to give a mixture of final products which can be separated chromatographically.

It is also possible to prepare the diastereomeric epoxyalcohols, which may be first separated by preparative chromatography, and each diastereomer may then be individually converted to its corresponding fluoroepoxide.

The gem-difluoro- and vinyl fluoro-containing compounds can be prepared via the alternative scheme described above, as follows:

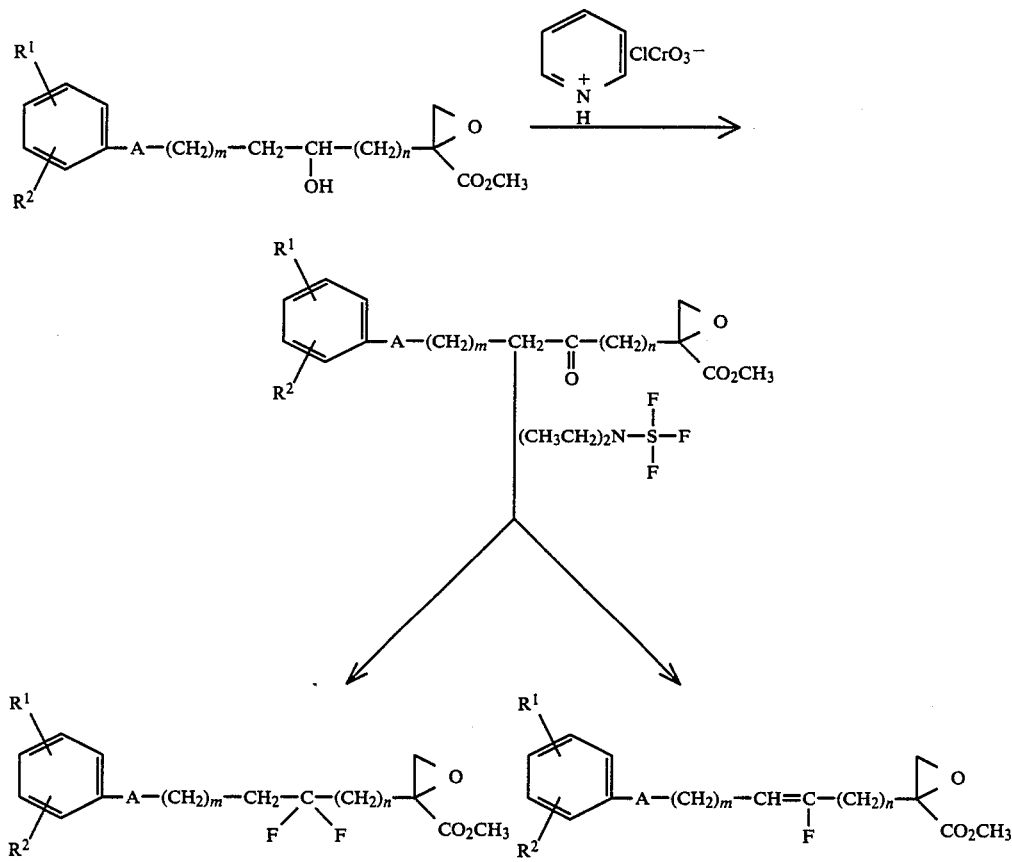

In the last step, the reaction of the ketone intermediate with the diethylaminosulfur trifluoride yields both the gem-difluoro- and vinyl fluoro-containing compounds, which are separated by preparative high pressure liquid chromatography.

The starting materials in the above preparative sequences are all commercially available or can be prepared by conventional methods as taught in the chemical literature.

The compounds of the invention, by virtue of their ability to inhibit carnitine palmitoyl transferase in hepatic mitochondria, exhibit hypoglycemic activity, and as such are indicated in the treatment of disorders based on glucose and fat metabolism disorders. Thus, the compounds can be used to treat manifest diabetes in adults and labile diabetes in young persons. The compounds can also be used in the control and alleviation of symptoms accompanying increased production of ketones. Equally importantly, the compounds of the invention, when compared to prior art fatty acid oxidation inhibitors of similar structure, demonstrate a very significantly reduced inhibition of fatty acid oxidation by heart mitochondria, thereby possessing the wholly unexpected and quite significant benefit of little or no potential for cardiotoxicity or impairment of normal cardiac function upon chronic administration.

When the compounds of the invention are employed as hypoglycemic agents, as in the treatment of diabetes, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The ability of the compounds of the invention to inhibit carnitine palmitoyl transferase in liver mitochondria and their significantly reduced potential for impairment of normal cardiac function may be demonstrated by known pharmacological procedures. The following examples show both the preparation and the pharmacological testing of compounds within the invention.

EXAMPLE 1

2-(1-Fluoro-5-phenylpentyl)-2-oxiranecarboxylic acid methyl ester

Method A (1) β-Hydroxy-α-methylenebenzeneheptanoic acid methyl ester (a) 5-phenyl-1-pentanal To a suspension of 20 g (93 mmol) of pyridinium chlorochromate in 300 ml of methylene chloride is added 9.9 g (60 mmol) of 5-phenyl-1-pentanol. The mixture is maintained at room temperature with vigorous stirring for 1.75 hours, diluted with ethyl ether and allowed to stand overnight. The mixture is filtered through Florisil with ethyl ether and rotoevaporated to give 8.4 g crude aldehyde which is used in the next reaction without further characterization.

(b) β-hydroxy-α-methylenebenzeneheptanoic acid methyl ester

A mixture of 8.4 g (52 mmol) of 5-phenylpentanal, 8.95 g (104 mmol) of methyl acrylate and 200 mg of 1,4-diazabicyclo[2.2.2]octane is allowed to stand at room temperature for 120 hours.

Rotoevaporation gives an oil which is purified chromatographically (silica gel; hexane:ethyl ether (3:2)) to afford 3.1 g of the title compound: IR (neat) γ 3440, 1715 cm$^{-1}$; NMR (CDCl$_3$) δ 1.28-1.74 (6H, m), 2.61 (2H, m), 2.61 (2H, t, J=8 Hz), 3.78 (3H, s), 4.39 (1H, t, J=8 Hz), 5.78 (1H, s), 6.23 (1H, s), 7.19 (3H, m) and 7.28 (2H, m).

Analysis for: C$_{15}$H$_{20}$O$_3$: Calculated: C, 72.55; H, 8.12. Found: C, 72.37; H, 8.09.

(2) 2-[1-Hydroxy-5-phenylpentyl]-2-oxiranecarboxylic acid methyl ester (isomer A)
2-[1-Hydroxy-5-phenylpentyl]-2-oxiranecarboxylic acid methyl ester (isomer B)

A solution of 11.2 g (45 mmol) of β-hydroxy-α-methylenebenzeneheptanoic acid methyl ester in 300 ml of 1,2-dichloroethane is treated with 200 mg of 4,4'-thiobis(6-t-butyl-m-cresol) and 24.5 g (138 mmol) of m-chloroperoxybenzoic acid. The mixture is heated to reflux under nitrogen for 26 hours.

The mixture is diluted with methylene chloride and is washed twice with aqueous saturated sodium sulfite. The combined methylene chloride layers are washed with aqueous sodium bicarbonate, dried over magnesium sulfate, filtered and rotoevaporated. The resultant oil is subjected to preparative HPLC (gradient elution-hexane:ethyl acetate (9:1) through ethyl acetate) to give 2.38 g of the more mobile isomer A (Rf 0.23 in hexane:ethyl ether (1:1)): IR (Neat) γ 3520 (broad), 1730 cm$^{-1}$; NMR (CDCl$_3$) δ 1.42-1.84 (6H, m), 2.31 (1H, broad d, removed by D$_2$O exchange), 2.64 (2H, t, J=7 Hz), 3.01 (1H, d, J=6 Hz), 3.15 (1H, d, J=6 Hz), 3.80 (3H, s), 3.86 (1H, broad m), 7.21 (3H, m) and 7.30 (2H, m):

Analysis for: C$_{15}$H$_{20}$O$_4$: Calculated: C, 68.16; H, 7.63. Found: C, 67.98; H, 7.53.
and 0.68 g of the less mobile (Rf 0.12 in hexane:ethyl ether (1:1)) isomer B: IR (neat) γ 3480 (broad), 1728 cm$^{-1}$; NMR (CDCl$_3$) δ 1.30-1.80 (6H, m), 2.11 (1H, broad s, removed by D$_2$O exchange), 2.63 (2H, t, J=7 Hz), 2.98 (1H, d, J=6Hz), 3.07 (1H, d, J=6 Hz) 3.76 (3H, s), 4.12 (1H, dd, J=3, 10 Hz), 7.20 (3H, m) and 7.30 (2H, m).

(3) 2-(1-Fluoro-5-phenylpentyl)-2-oxiranecarboxylic acid methyl ester (isomer A)

To a solution of 2.44 g (15 mmol; 2.0 ml) of diethylaminosulfur trifluoride in 50 ml of methylene chloride cooled to −78° C. under a nitrogen atmosphere is added dropwise a solution of 2.00 g (7.6 mmol) of 2-[1-hydroxy-5-phenylpentyl]-2-oxiranecarboxylic acid methyl ester (isomer A) in 50 ml of methylene chloride over 30 minutes. The mixture is stirred at −78° C. for 90 minutes and then is allowed to come to room temperature. The mixture is stirred at room temperature for 1.5 hours, is quenched with a saturated aqueous solution of sodium bicarbonate and is extracted with ethyl ether. The combined ethereal extracts are dried over magnesium sulfate, filtered and rotoevaporated. The resulting oil is purified chromatographically (silica gel; hexane:ethyl acetate (9:1)) to give 1.19 g of the title compound (Rf 0.54 in hexane:ethyl ether (3:2)): IR (neat) γ 1750 cm$^{-1}$; NMR (CDCl$_3$) δ 1.40-1.96 (6H, m), 2.64 (2H, t, J=8 Hz), 3.07 (1H, dd, J=4, 6 Hz), 3.15 (1H, d, J=6 Hz), 3.15 (1H, d, J=6 Hz), 3.79 (3H, s), 5.14 (1H, ddd, J$_{HF}$=48 Hz, J=10, 3 Hz), 7.21 (2H, d, J=8 Hz) and 7.31 (2H, d, J=8 Hz).

Analysis for: C$_{15}$H$_{19}$FO$_3$: Calculated: C, 67.67; H, 7.14. Found: C, 67.73; H, 7.30

Method B (1) β-Fluoro-α-methylenebenzeneheptanoic acid methyl ester

To a solution of 1.93 g (12 mmol; 1.47 ml) of diethylaminosulfur trifluoride in 30 ml of methylene chloride cooled to −78° C. under a nitrogen atmosphere is added over 30 minutes a solution of 1.49 g (6 mmol) of β-hydroxy-α-methylene-benzeneheptanoic acid methyl ester of Method A, step 1 above, in 30 ml of methylene chloride. After 30 minutes at −78° C., the solution is allowed to rise to room temperature and is maintained with stirring for 1.5 hours.

The solution is diluted with brine and extracted with methylene chloride. The combined organic extracts are washed with brine, dried over magnesium sulfate, filtered and rotoevaporated to give crude product.

Column chromatography on silica gel (hexane:ethyl ether (4:1)) gives 797 ml of the title compound: IR (neat) γ 1721 cm$^{-1}$; NMR (CDCl$_3$) δ 1.28-1.88 (6H, m), 2.52 (2H, t, J=8 Hz), 3.66 (3H, s), 5.2 (1H, ddd, J$_{HF}$=48 Hz and J=3, 9 Hz), 5.83 (1H, s) 6.25 (1H, d, J=3 Hz), 7.09 (3H, m), 7.19 (2H, d, J=8 Hz).

Analysis for: C$_{15}$H$_{19}$FO$_2$: Calculated: C, 71.97; H, 7.65. Found: C, 72.07; H, 7.71.

(2) 2-(1-Fluoro-5-phenylpentyl)-2-oxiranecarboxylic acid methyl ester (isomer A)
2-(1-Fluoro-5-phenylpentyl)-2-oxiranecarboxylic acid methyl ester (isomer B)

A solution of 500 mg (2.0 mmol) of β-fluoro-α-methylenebenzeneheptanoic acid methyl ester in 50 ml of 1,2-dichloroethane is treated with 1.38 g (8 mmol) of m-chloroperoxybenzoic acid and 20 mg of 4,4'-thiobis(6-t-butyl-m-cresol). The mixture is heated to reflux and maintained under nitrogen for 10.5 hours. An additional 1.38 g (8 mmol) of m-chloroperoxybenzoic acid and 20 mg of 4,4'-thiobis(6-t-butyl-m-cresol) is added and reflux is continued for 8 hours.

The mixture is diluted with ethyl ether and washed sequentially with aqueous sodium sulfite, aqueous sodium bicarbonate, aqueous sodium sulfite and finally aqueous sodium bicarbonate. The ethereal solution is dried over magnesium sulfate, filtered and evaporated.

The residue is chromatographed preparatively on silica gel (hexane:ethyl ether (3:1)) to give the title compound of Example 1 (isomer A) (Rf 0.37 in hexane:ethyl ether (3:2)) and isomer B (Rf 0.25 in hexane:ethyl ether (3.2)): IR (neat) γγ 1742 cm$^{-1}$; NMR (CDCl$_3$) δ 1.40–1.88 (6H, m), 2.64 (2H, t, J=8 Hz), 2.94 (1H, d, J=6 Hz), 3.13 (1H, dd, J=6 Hz, J$_{HF}$=3 Hz), 3.81 (3H, s), 4.93 (1H, ddd, J$_{HF}$=48 Hz, J=10, 3 Hz), 7.20 (2H, d, J=8 Hz) and 7.31 (2H, d, J=8 Hz).

EXAMPLE 2

2-[5-(4-Chlorophenoxy)-1-fluoropentyl]-2-oxiranecarboxylic acid methyl ester

Method A (1)

β-Hydroxy-α-methylene-7-(4-chlorophenoxy)heptanoic acid methyl ester (a) 5-(4-chlorophenoxy)-1-pentanal To a suspension of 33 g (0.15 mmol) of pyridinium chlorochromate in 450 ml of methylene chloride is added 21.4 g (0.1 mmol) of 5-(4-chlorophenoxy)-1-pentanol. The mixture is maintained with stirring for 3 hours, diluted with 900 ml of ethyl ether and stirred for an additional 1 hour.

The mixture is filtered through Florisil to give after rotoevaporation 18.2 g of the title product: IR (neat) 1728, 1493 and 1248 cm$^{-1}$.

(b)

β-hydroxy-α-methylene-7-(4-chlorophenoxy)heptanoic acid methyl ester

A mixture of 18.0 g (84.6 mmol) of 5-(4-chlorophenoxy)-1-pentanal, 10.9 g (127 mmol) of methyl acrylate and 1.1 g (10 mmol) of 1,4-diazabicyclo[2.2.2]octane is allowed to stand at room temperature for 139 hours.

The excess methyl acrylate is removed from the mixture under a stream of nitrogen and by rotoevaporation. The residual oil is partitioned between ice-cold aqueous 10% hydrochloric acid and ethyl ether. The combined ethereal extracts are washed with ice-cold aqueous 10% hydrochloric acid, dried over magnesium sulfate, filtered and rotoevaporated to give crude product.

Column chromatography on silica gel using hexane:ethyl ether (3:2) as eluent gives 10.3 g of title compound: IR (neat) γ 3460 (broad), 1715, 1491 and 1242 cm$^{-1}$; NMR (CDCl$_3$) δ 1.42–1.94 (6H, m), 2.54 (1H, broad s removed by D$_2$O exchange), 3.78 (3H, s), 3.94 (2H, t, J=7 Hz), 4.45 (1H, t, J=7 Hz), 5.84 (1H, s), 6.27 (1H, s), 6.83 (2H, d, J=8 Hz) and 7.24 (2H, d, J=8 Hz).

(2)

2-[5-(4-Chlorophenoxy)-1-hydroxypentyl]-2-oxiranecarboxylic acid methyl ester (isomer A)

2-[5-(4-Chlorophenoxy)-1-hydroxypentyl]-2-oxiranecarboxylic acid methyl ester (isomer B)

A solution of β-hydroxy-α-methylene-5-(4-chlorophenoxy)heptanoic acid methyl ester (10.3 g; 34.5 mmol) in 100 ml of 1,2-dichloroethane is treated with 100 mg of 4,4'-thiobis(6-t-butyl-m-cresol) and 12.1 g (700 mmol) of m-chloroperoxybenzoic acid. The mixture is heated to reflux under nitrogen for 17 hours.

The mixture is cooled, treated with 10% aqueous sodium sulfite and extracted with ethyl ether. The ethereal extract is washed with aqueous sodium bicarbonate, 10% aqueous sodium sulfite and aqueous sodium bicarbonate. The organic extract is dried over magnesium sulfate, filtered and rotoevaporated to give an oil as a 3:1 mixture (isomer A:isomer B) of the diastereomeric title compounds.

The mixture is separated chromatography (silica gel; hexane:ethyl ether (3:2)) to give 1.38 g of isomer A (Rf 0.16 in hexane:ethyl ether (1:1)); IR (neat) γ 3520 (broad), 1739, 1493, and 1247 cm$^{-1}$; NMR (CDCl$_3$) δ 1.54–1.71 (2H, m), 1.71 (4H, m), 2.38 (1H, broad s, removed on D$_2$O exchange), 3.03 (1H, d, J=6 Hz) 3.17 (1H, d, J=6 Hz), 3.80 (3H, s), 3.91 (1H, m), 3.97 (2H, t, J=6 Hz), 6.85 (2H, d, J=10 Hz), 7.26 (2H, d, J=10 Hz).

Analysis for: C$_{15}$H$_{19}$ClO$_5$: Calculated: C, 57.23; H, 6.08. Found: C, 56.86; H, 5.99. and 0.46 g of isomer B (Rf 0.10 in hexane:ethyl ether (1:1)): IR (neat) γ 3480 (broad), 1738, 1497 and 1249 cm$^{-1}$; NMR (CDCl$_3$) δ 1.52–1.96 (6H, m), 2.12 (1H, broad s, removed by D$_2$O exchange), 3.04 (1H, d, J=6 Hz), 3.14 (1H, d, J=8 Hz), 3.80 (3H, s), 3.96 (2H, t, J=6 Hz), 4.18 (1H, m), 6.85 (2H, d, J=9 Hz), 7.16 (2H, d, J=9 Hz).

Analysis for: C$_{13}$H$_{19}$ClO$_5$: Calculated: C, 57.23; H, 6.08. Found: C, 56.69; H, 6.26.

(3)

2-[5-(4-Chlorophenoxy-1-fluoropentyl]-2-oxiranecarboxylic acid methyl ester (isomer A)

To a solution of 967 mg (6 mmol, 733 μl) of diethylaminosulfur trifluoride in 25 ml of methylene chloride cooled to −78° C. under a nitrogen atmosphere is added dropwise a solution of 945 mg (3 mmol) of 2-[5-(4-chlorophenoxy)-1-hydroxypentyl]-2-oxiranecarboxylic acid methyl ester (isomer A) in 25 ml of methylene chloride over 30 minutes. The mixture is stirred at −78° C. for 30 minutes and then is allowed to come to room temperature. The mixture is stirred at room temperature for 1.5 hours, is quenched with brine and is extracted with ethyl ether. The combined ethereal extracts are dried over magnesium sulfate, filtered and rotoevaporated to give a crude solid. Trituration with cyclohexane:isopropyl ether and subsequent high vacuum drying affords 597 mg of the title compound (isomer A) (Rf 0.45 in hexane:ethyl ether (1:1)): m.p. 76°–78° C.; IR (KBr) γ 1740, 1497, 1257, 832 and 758 cm$^{-1}$; NMR (CDCl$_3$) δ 1.54–2.02 (6H, m), 3.10 (1H, dd, J=3, 6 Hz), 3.18 (1H, d, J=6 Hz), 3.80 (3H, s), 3.96 (2H, t, J=7 Hz), 5.19 (1H, ddd, J$_{HF}$=48 Hz, J=3, 10 Hz), 6.85 (2H, d, J=7 Hz) and 7.27 (2H, d, J=7 Hz).

Analysis for: C$_{15}$H$_{18}$FClO$_4$: Calculated: C, 56.88; H, 5.73. Found: C, 55.82; H, 5.65.

2-[5-(4-Chlorophenoxy)-1-fluoropentyl]-2-oxiranecarboxylic acid methyl ester (isomer B)

To a solution of 1.03 g (6.36 mmol, 777 μl) of diethylaminosulfur trifluoride in 25 ml of methylene chloride cooled to −78° C. under a nitrogen atmosphere is added dropwise over 5 minutes a solution of 1.0 g (3.18 mmol) of 2-[5-(4-chlorophenoxy)-1-hydroxypentyl]-2-oxiranecarboxylic acid methyl ester (isomer B) in 10 ml of methylene chloride. The mixture is allowed to warm to room temperature and is stirred for 1.5 hours.

The mixture is cooled in an ice bath and is quenched dropwise with aqueous sodium bicarbonate. The solution is extracted with ethyl ether, and the combined ethereal extracts are dried over magnesium sulfate. Filtration and rotoevaporation gives 1.0 g of crude product which is subjected to preparative column chromatography on silica gel (hexane:ethyl ester (7:3)). The appropriate fractions ($R_f$ 0.23 (hexane:ethyl ether (3:2)) are combined and rotoevaporated to give 555 mg (55.1%) of the title compound: IR (film) 1730 cm$^{-1}$; NMR (CDCl$_3$) δ 1.54–1.96 (6H, mc), 2.97 (1H, d, J=6 Hz), 3.16 (1H, dd, J=6, 2 Hz), 3.83 (3H, s), 3.97 (2H, t, J=8 Hz), 4.98 (1H, ddd, $J_{HF}$=48 Hz, 10, 2 Hz), 6.85 (2H, d, J=10 Hz), 7.28 (2H, d, J=10 Hz).

Analysis for: C$_{15}$H$_{18}$ClFO$_4$: Calculated: C, 56.88; H, 5.73. Found: C, 56.34; H, 5.66.

EXAMPLE 3

2-[6-(4-Chlorophenoxy)-1-fluorohexyl]-2-oxiranecarboxylic acid methyl ester

Method A (1)

β-Hydroxy-α-methylene-8-(4-chlorophenoxy)octanoic acid methyl ester (a) 6-(4-chlorophenoxy)-1-hexanal To a suspension of 32 g (0.15 mol) of pyridinium chlorochromate in 450 ml of methylene chloride is added 23 g (0.1 mol) of 6-(4-chlorophenoxy)-1-hexanol. The mixture is maintained under a nitrogen atmosphere for 2 hours, is diluted with 1000 ml of ethyl ether and is stirred for 1.5 hours.

The mixture is filtered through a column of Florisil and neutral alumina using ethyl ether for elution. Rotoevaporation gave 18.9 of the title compound which is used without characterization.

(b)

β-hydroxy-α-methylene-8-(4-chlorophenoxy)octanoic acid methyl ester

A mixture of 18.9 g (0.083 mol) of 6-(4-chlorophenoxy)-1-hexanal, 21.5 g (0.25 mol) of methyl acrylate and 500 mg of 1,4-diazabicyclo[2.2.2]octane is allowed to stand at room temperature for 112.5 hours (an additional 500 mg of 1,4-diazabicyclo-[2.2.2]octane is added after 66 hours and 96 hours). Excess methyl acrylate is removed under a stream of nitrogen to give a crude oil.

Column chromatography on silica gel (hexane:ethyl ether (3:2)) yields 2.7 g of the title compound.

An analytical sample is obtained by preparative layer chromatogrpahy (Rf 0.14 in hexane:ethyl ether (3:2)): IR (neat) γ 1713, 1490, 1241 and 819 cm$^{-1}$; NMR (CDCl$_3$) δ 1.30–1.98 (8H, s), 3.93 (2H, t, J=8 Hz), 4.42 (1H, t, J=7 Hz), 5.83 (1H, s), 6.26 (1H, s), 6.84 (2H, d, J=9 Hz), and 7.25 (2H, d, J=9 Hz).

Analysis for: C$_{16}$H$_{20}$ClO$_4$: Calculated: C, 61.63; H, 6.47. Found: C, 61.40; H, 6.67.

(2)

2-[6-(4-Chlorophenoxy)-1-hydroxyhexyl]-2-oxiranecarboxylic acid methyl ester (isomer A)

A solution of 1.5 g (5.0 mmol) of β-hydroxy-α-methylene-8-(4-chlorophenoxy)octanoic acid methyl ester in 50 ml of 1,2-dichloroethane is treated with 25 mg of 4,4'-thiobis(6-t-butyl-m-cresol) and 1.73 g (10 mmol) of m-chloroperoxybenzoic acid. The mixture is stirred at room temperature for 2.5 hours. The mixture is heated to reflux under a nitrogen atmosphere and is maintained for 15.5 hours.

The mixture is diluted with methylene chloride and then is washed sequentially with aqueous sodium sulfite and aqueous sodium bicarbonate. The sodium sulfite and sodium bicarbonate washes are repeated and the organic layer is finally dried over magnesium sulfate. Filtration and rotoevaporation gives an oil which is subjected to preparative column chromatography (silica gel; hexane:ethyl ether (1:1)) to give 480 mg of the title compound (isomer A; Rf 0.20 in hexane:ethyl ether (1:1)): NMR (CDCl$_3$) δ 1.22–1.86 (8H, m), 3.01 (1H, d, J=6 Hz), 3.16 (1H, d, J=6 Hz), 3.80 (3H, s), 3.89 (1H, m), 3.92 (2H, t, J=7 Hz), 6.84 (2H, d, J=9 Hz) and 7.25 (2H, d, J=9 Hz).

(3)

2-[6-(4-chlorophenoxy)-1-fluorohexyl]-2-oxiranecarboxylic acid methyl ester (isomer A)

To a solution of 474 mg (2.94 mmol; 359 μl) of diethylaminosulfur trifluoride in 25 ml of methylene chloride cooled to −78° C. under nitrogen atmosphere in 25 ml of methylene chloride cooled to −78° C. under a nitrogen atmosphere is added dropwise over 45 minutes a solution of 480 mg (1.47 mmol) of 2-[6-(4-chlorophenoxy)-1-hydroxyhexyl]-2-oxiranecarboxylic acid methyl ester in 25 ml of methylene chloride. The solution is maintained at −78° C. with stirring for 1.25 hours and then is allowed to warm to room temperature. After 1 hour the solution is quenched with 25 ml of aqueous saturated sodium bicarbonate and is stirred for 30 minutes.

The mixture is then diluted with aqueous sodium bicarbonate and is extracted with ethyl ether. The combined ethereal extracts are dried over magnesium sulfate, filtered and rotoevaporated to give crude product. Column chromatography (silica gel; hexane:ethyl ether (7.3)) affords 432 mg of the title compound (isomer A; Rf 0.32 in hexane:ethyl ether (3:2)): IR (neat) γ 1735, 1490, and 1242 cm$^{-1}$; NMR (CDCl$_3$) δ 1.42–2.00 (8H, m), 3.09 (1H, dd, J=7, 5 Hz), 3.17 (1H, d, J=7 Hz), 3.80 (3H, s), 3.95 (2H, t, J=6 Hz), 5.18 (1H, ddd, $J_{HF}$=48 Hz, J=9, 4 Hz) and 6.85 (2H, d, J=9 Hz).

Analysis for: C$_{16}$H$_{20}$ClFO$_4$: Calculated: C, 58.09; H, 6.09. Found: C, 57.56; H, 6.08.

2-[6-(4-Chlorophenoxy)-1-fluorohexyl]-2-oxiranecarboxylic acid methyl ester (isomer B)

To a solution of 1.77 g (10.96 mmol, 1.45 ml) of diethylaminosulfur trifluoride in 95 ml of methylene chloride cooled to −78° C. under nitrogen is added dropwise a solution of 1.80 g (5.48 mmol) of 2-[6-(4-chlorophenoxy)-1-hydroxyhexyl]-2-oxiranecarboxylic acid methyl ester (isomer B) over 60 minutes. The mixture is stirred at −78° C. for 75 minutes, is allowed to come to room temperature over 1 hour and is stirred for an additional 1 hour. The mixture is quenched at 0° C. by dropwise addition of aqueous sodium bicarbonate and is stirred for 30 minutes. Dilution with aqueous sodium bicarbonate and extraction with ethyl ether affords, after drying over magnesium sulfate, filtration and rotoevaporation of the combined ethereal extracts, crude product.

Column chromatography on silica gel (hexane:ethyl ether (7:3)) gives 0.25 g (13.8%) of the title compound: IR (film) 1740 cm$^{-1}$ NMR (CDCl$_3$) δ 1.42–1.92 (8H, mc), 2.97 (1H, d, J=6 Hz), 3.16 (1H, dd, J=6, 3 Hz), 3.84 (3H, s), 3.96 (2H, t, J=8 Hz), 4.97 (1H, ddd, $J_{HF}$=48, 10, 2 Hz), 6.86 (2H, d, J=10 Hz), 7.28 (2H, d, J=10 Hz).

Analysis for: $C_{16}H_{20}ClFO_4$; Calculated: C, 58.09; H, 6.09. Found: C, 57.50; H, 6.10.

EXAMPLE 4

2-[5-(4-Chlorophenoxy)-1-fluoropentyl]-2-oxiranecarboxylic acid sodium salt (isomer A)

A solution of 2-[5-(4-chlorophenoxy)-1-fluoropentyl]-2-oxiranecarboxylic acid methyl ester (2.53 g, 8 mmol) of Example 2 in 25 ml of absolute ethanol is treated with a solution of 320 mg (8 mmol) of sodium hydroxide in 12 m l of water. The mixture is maintained with stirring at room temperature for 2 hours and then is rotoevaporated. The obtained solid is triturated three times with ethyl ether, the solvent is removed by roto-evaporation and the solid is dried at high vacuum over phosphorus pentoxide to give 2.25 g (86.6%) of the title compound: m.p. 159°–175° C.; IR (KBr) 1630, 1608, 1490 and 1242 cm$^{-1}$; NMR (d$_6$-DMSO) δ 1.54 (2H, m), 1.73 (4H, m), 1.73 (4H, m), 2.65 (1H, m), 2.73 (1H, d, J=6 Hz), 3.98 (2H, t, J=6 Hz), 5.22 (1H, ddd, $J_{HF}$=48, 10, 3 Hz), 7.00 (2H, d, J=9 Hz) and 7.36 (2H, d, J=9 Hz).

Analysis for: $C_{14}H_{15}NaFClO_4$; Calculated: C, 51.78; H, 4.66. Found: C, 51.37; H, 4.53.

EXAMPLE 5

2-[6-(4-Chlorophenoxy)-1-fluorohexyl]-2-oxiranecarboxylic acid sodium salt (isomer A)

To a suspension of 1.79 g (5.41 mmol) of 2-[6-(4-chlorophenoxy)-1-fluorohexyl]-2-oxiranecarboxylic acid methyl ester (isomer A) of Example 3 in 5.14 ml of absolute ethanol is added at room temperature 5.14 ml (5.14 mmol) of 1N aqueous sodium hydroxide. After 30 minutes, 4.0 ml of tetrahydrofuran is aded to achieve total dissolution and stirring is maintained for 1.25 hours. Evaporation of the solvents and trituration with pentane and isopropyl ether gives 1.46 g (79.7%) of the title compound: m.p. 112°–125° C.; IR (KBr) 1640, 1608 cm$^{-1}$; NMR (d$_6$-DMSO) δ 1.47 (4H, m), 1.74 (4H, m), 2.63 (1H, dd, J=8, 3 Hz), 2.73 (1H, d, J=8 Hz), 3.98 (2H, t, J=9 Hz), 5.19 (1H, ddd, J=48, 10, 2 Hz), 6.98 (2H, d, J=8 Hz).

Analysis for: $C_{15}H_{17}ClFO_4Na$: Calculated: C, 53.19; H, 5.06. Found: C, 51.22; H, 5.03.

EXAMPLE 6

2-[5-(4-Chlorophenoxy)-1,1-difluoropentyl]-2-oxiranecarboxylic acid methyl ester
2-[5-(4-Chlorophenoxy)-1-fluoro-1-pentenyl]-2-oxiranecarboxylic acid methyl ester (1)
2-[5-(4-Chlorophenoxy)-1-oxopentyl]-2-oxiranecarboxylic acid methyl ester To a suspension of 9.05 g (42 mmol) of pyridinium chlorochromate and 3.4 g (42 mmol) of sodium acetate in 150 ml of methylene chloride is added 2.2 g (7 mmol) of 2-[5-(4-chlorophenoxy)-1-hydroxypentyl]-2-oxiranecarboxylic acid methyl ester of Example 2, part 2. The mixture is stirred for 4 hours, is diluted with ethyl ether and is filtered through Florisil. The solution is rotoevaporated and is chromatographed preparatively on silica gel using hexane:ethyl ether (3:2) as eluting solvent. The appropriate fractions are combined, washed with aqueous copper sulfate and brine and dried over magnesium sulfate. Filtration and roto-evaporation gives crude product. Column chromatography (silica gel; hexane:ethyl ether (3:2)) affords 523 mg (23.9%) of the title compound: IR (film) 1746, 1717 cm$^{-1}$; NMR (CDCl$_3$) δ 1.80 (4H, m), 2.66 (2H, m), 3.08 (1H, d, J=6 Hz), 3.34 (1H, d, J=6 Hz), 3.84 (3H, s), 3.94 (2H, t, J=6 Hz), 6.82 (2H, d, J=10 Hz) and 7.24 (2H, d, J=10 Hz).

Analysis for: $C_{15}H_{17}ClO_5$: Calculated: C, 57.60; H, 5.48. Found: C, 57.41; H, 5.56.

(2)
2-[5-(4-Chlorophenoxy-1,1-difluoropentyl]-2-oxiranecarboxylic acid methyl ester
2-[5-(4-Chlorophenoxy)-1-fluoro-1-pentenyl]-2-oxiranecarboxylic acid methyl ester To a solution of 6.48 g (40 mmol, 5.31 ml) of diethylaminosulfur trifluoride in 50 ml of anhydrous glyme is added at room temperature 3.13 g (10 mmol) of 2-[5-(4-chlorophenoxy)-1-oxopentyl]-2-oxiranecarboxylic acid methyl ester. The mixture is heated in an oil bath maintained at 110° C. for 4 hours.

The mixture is cooled to ice-bath temperature and is quenched with aqueous ice-cold sodium bicarbonate. The mixture is extracted with ethyl ether and the combined ethereal extracts are dried over magnesium sulfate, filtered and roto-evaporated to give crude products.

The crude material is subjected to preparative HPLC (gradient elution from hexane through hexane:ethyl acetate (95:5)) twice to give 551 mg (16.5%) of 2-[5-(4-chlorophenoxy)-1,1-difluoropentyl]-2-oxiranecarboxylic acid methyl ester (R$_f$ 0.47 hexane:ethyl ether (1:1)): m.p. 40°–48° C., IR (KBr) 1741 cm$^{-1}$; NMR (CDCl$_3$) δ 1.75 (2H, m), 1.85 (2H, m), 2.29 (2H, m), 3.16 (1H, dd, J=6, 2 Hz), 3.23 (1H, d, J=6 Hz), 3.84 (3H, s), 3.97 (2H, t, J=7 Hz), 6.85 (2H, d, J=9 Hz), 7.28 (2H, d, J=9 Hz):

Analysis for: $C_{15}H_{17}ClF_2O_4$: Calculated: C, 53.82; H, 5.12. Found: C, 53.66; H, 5.06.

and 487 mg (15.5%) of oil 2-[5-(4-chlorophenoxy)-1-fluoro-1-pentenyl]-2-oxiranecarboxylic acid methyl ester (R$_f$ 0.42 in hexane:ethyl ether (1:1)): IR (film) 1748, 1488 and 1240 cm$^{-1}$; NMR (CDCl$_3$) δ 1.89 (2H, p, J=9 Hz), 2.37 (2H, m), 3.12 (1H, d, J=7 Hz), 3.29 (1H, dd, J=7, 2 Hz), 3.82 (3H, s), 3.96 (2H, t, J=6 Hz), 5.24 (1H, dt, J=36, 8 Hz), 6.85 (2H, d, J=8 Hz) and 7.27 (2H, d, J=8 Hz).

Analysis for: $C_{15}H_{16}ClFO_4$: Calculated: C, 57.24; H, 5.12. Found: C, 56.90; H, 4.95.

EXAMPLE 7

2-[6-(4-Chlorophenoxy)-1,1-difluorohexyl]-2-oxiranecarboxylic acid methyl ester
2-[6-(4-Chlorophenoxy)-1-fluoro-1-hexenyl]-2-oxiranecarboxylic acid methyl ester (1)
2-(6-(4-Chlorophenoxy)-1-oxohexyl]-2-oxiranecarboxylic acid methyl ester To a suspension of 11.6 g (54 mmol) of pyridinium chlorochromate and 4.4 g (54 mmol) of sodium acetate in 200 ml of methylene chloride is added 2.95 g (9 mmol) of 2-([6-(4-chlorophenoxy)-1-hydroxyhexyl]-2-oxiranecarboxylic acid methyl ester (isomer A) prepared according to the procedure of Example 2, part 2, at room temperature under a nitrogen atmosphere. The mixture is stirred for 4 hours, is diluted with 600 ml of ethyl ether and is filtered through Florisil. Rotoevaporation gives 2.2 g of crude product. Preparative column chromatography (silica gel; hexane:ethyl ether (3:2)) affords 1.66 g (56.4%) of the title compound: IR (film) 1746, 1719 cm$^{-1}$; NMR (CDCl$_3$) δ 1.49 (2H, p, J=8 Hz), 1.62–1.86 (4H, mc), 2.62 (2H, m), 3.05 (1H, d, J=6 Hz), 3.36 (1H, d, J=6 Hz), 3.86 (3H, s), 3.94 (2H, t, J=6 Hz), 6.84 (2H, d, J=8 Hz) and 7.27 (2H, d, J=8 Hz).

Analysis for: C$_{16}$H$_{19}$ClO$_5$: Calculated: C, 58.81; H, 5.86. Found: C, 58.99; H, 5.80

(2)
2-[6-(4-Chlorophenoxy)-1,1-difluorohexyl]-2-oxiranecarboxylic acid methyl ester
2-[6-(4-Chlorophenoxy)-1-fluoro-1-hexenyl]-2-oxiranecarboxylic acid methyl ester To a solution of 1.29 (8 mmol), 1.06 ml) of diethylaminosulfur trifluoride in 50 ml of anhydrous glyme is added 1.31 g (4 mmol) of 2-[6-(4-chlorophenoxy)-1-oxohexyl]-2-oxiranecarboxylic acid methyl ester. The mixture is heated to reflux under nitrogen for 2.5 hours. An additional 2.58 g (16 mmol, 2.1 ml) of diethylaminosulfur trifluoride is added and reflux is continued for 5.5 hours. The mixture is allowed to come to room temperature for 16 hours and is then heated to reflux for 3 hours. The mixture is cooled to ice-bath temperature and is quenched dropwise with saturated aqueous sodium bicarbonate. The mixture is extracted with ethyl ether and the combined ethereal extracts are dried over magnesium sulfate. Filtration and rotoevaporation gives an oil which crystallizes upon overnight refrigeration. The solid is triturated and crystallized from hexane:cyclohexane (1:1) to give a crude solid (m.p. 44°–46° C.).

Flash chromatography on silica gel (230–400 mesh) utilizing hexane:benzene:ethyl acetate (12:5:2) as eluting solvent gives 250 mg (23.3%) of 2-[6-(4-chlorophenoxy)-1,1-difluorohexyl]-2-oxiranecarboxylic acid methyl ester (R$_f$ 0.54 in hexane:ethyl ether (1:1): m.p. 54°–55° C.; IR (KBr) 1740 cm$^{-1}$; NMR (CDCl$_3$) δ 1.79 (6H, mc), 1.83 (2H, p, J=8 Hz), 2.26 (2H, m), 3.16 (1H, dd, J=6, 2 Hz), 3.24 (1H, J=6 Hz), 3.85 (3H, s), 3.96 (2H, t, J=8 Hz), 6.86 ) (2H, d, J=10 Hz) and 7.48 (2H, d, J=10 Hz):

Analysis for: C$_{16}$H$_{19}$ClF$_2$O$_4$: Calculated: C, 55.10; H, 5.49. Found: C, 55.03; H, 5.47.
and a crude oil which is subjected sequentially to preparative flash chromatography (silica gel; hexane:benzene:ethyl acetate (13:6:1)) and preparative layer chromatography (silica gel; toluene:hexane (9:1)). Obtained is 63 mg (4.8%) of 2-[6-(4-chlorophenoxy)-1-fluoro-1-hexenyl]-2-oxiranecarboxylic acid methyl ester (R$_f$ 0.46 in hexane:ethyl ether (1:1)): IR (film) 1740 cm$^{-1}$; NMR (CDCl$_3$) δ 1.60 (2H, m), 1.82 (2H, m), 2.27 (2H, m), 3.14 (1H, d, J=6 Hz), 3.29 (1H, dd, J=6, 2 Hz), 3.86 (3H, s), 3.96 (2H, t, J=7 Hz), 5.22 (1H, dt, J$_{HF}$=36, J=7 Hz), 6.85 (2H, d, J=9 Hz), 7.28 (2H, d, J=9 Hz).

Analysis for: C$_{16}$H$_{18}$ClFO$_4$: Calculated: C, 58.45; H, 5.52. Found: C, 58.52; H, 5.56.

EXAMPLE 8

2-[6-(4-Chlorophenoxy)-1,1-difluorohexyl]-2-oxiranecarboxylic acid sodium salt

A solution of 348 mg (1 mmol) of 2-[6-(4-chlorophenoxy)-1,1-difluorohexyl]-2-oxiranecarboxylic acid methyl ester of Example 7 in 10 ml of 95% ethanol is treated with a solution of 40 mg (1 mmol) of sodium hydroxide in 5 ml of water. The solution is stirred at room temperature for 3 hours and is then roto-evaporated. The obtained solid is triturated two times with ethyl ether and the solvent is removed to give 289 mg (77.1%) of the title compound: m.p. 140°–153° C.; IR (KBr) 1645; 1618 cm$^{-1}$; NMR (d$_6$-DMSO) δ 1.46 (4H, m), 1.73 (2H, p, J=7 Hz), 2.42 (2H, m), 2.70 (1H, d, J=7 Hz), 2.76 (1H, d, J=7 Hz), 3.98 (2H, t, J=7 Hz), 7.00 (2H, d, J=10 Hz) and 7.36 (2H, d, J=10 Hz).

Analysis for: C$_{15}$H$_{16}$ClF$_2$NaO$_4$: Calculated: C, 48.07; H, 4.84. Found: C, 48.13; H, 4.47.

EXAMPLE 9

The following assay measures the ability of the compounds of the invention to inhibit the activity of carnitine palmitoyl transferase in liver and heart mitochondria.

According to this procedure, the following steps are carried out:

(1) Isolation of Mitochondria (a) liver mitochondria: 5 g of liver from a 300 g rat is minced, homogenized with 40 ml (30 ml for heart mitochondria) of 0.25M sucrose, 10 mM Tris and 1 mM EDTA, pH 7.4 and centrifuged at 600 xg for 15 minutes. The decanted supernatant is centrifuged at 7,900 xg for 15 minutes. The resultant pellet is resuspended in 20 ml total (16 ml total for the heart mitochondria) of sucrose buffer and centrifuged 7,900 xg for 15 minutes. The pellet is then resuspended in 30 ml total (11 ml for heart mitochondria) of 0.15M KCl, 5 mM Tris.Cl, pH 7.4 and this is used as the enzyme source.

(b) heart mitochondria: four rat hearts are processed as described in step (a) above to obtain a heart mitochondria fraction.

(2) Reaction Mixture

To 28 3 ml glass test tubes is added 350 μl of the following mixture:

0.15 ml of 200 mM ATP
0.03 ml of 1M MgCl$_2$
0.171 ml of 50 mM GSH
0.720 ml of 3M KCl
0.188 ml of 1M Tris
81 mg of FFA free albumin
0.435 ml of 100 mM of KCN
7.3 ml of H$_2$O
1.5 ml of 0.5 mM palmitoyl CoA Then there are added to these test tubes 50 μl of water, 50 μl of 10 mM carnitine and 0.25 μCi$^3$H-carnitine, and the tubes are placed in a 30° C. water bath.

(3) Mitochondrial Suspensions

Twelve plastic incubation tubes are prepared by adding the following to the tubes:

| Tube 1 | .15 ml H$_2$O + .05 ml DMSO |
| Tube 2 | .05 ml H$_2$O + .05 ml DMSO |
| Tube 3 | .19 ml H$_2$O + .01 ml 1 mM inhibitor to be tested |
| Tube 4 | .05 ml H$_2$O + .05 ml .001 mM inhibitor to be tested |
| Tube 5 | .09 ml H$_2$O + .01 ml .01 mM inhibitor to be tested |
| Tube 6 | .05 ml H$_2$O + .05 ml .01 mM inhibitor to be tested |
| Tube 7 | .09 ml H$_2$O + .01 ml .1 mM inhibitor to be tested |
| Tube 8 | .08 ml H$_2$O + .02 ml .1 mM inhibitor to be tested |
| Tube 9 | .05 ml H$_2$O + .05 ml .1 mM inhibitor to be tested |
| Tube 10 | .09 ml H$_2$O + .01 ml 1 mM inhibitor to be tested |
| Tube 11 | .05 ml H$_2$O + .05 ml 1 mM inhibitor to be tested |
| Tube 12 | .05 ml H$_2$O + .05 ml 1 mM prior art compound |

To each of the tubes, except 1 and 3, are added 30 μl of 200 mM ATP, 20 μl of 333 mM MgCl$_2$ and 50 μl of 1.5 mg/ml CoA. 800 μl of mitochondria from step (1) above are added to each tube, and the tubes are incubated at room temperature for 20 minutes. The tubes are centrifuged at 7,900 xg for 3 minutes and the resultant pellet is resuspended in 1 ml chilled 150 mM KCl, 5 mM TRIS, pH 7.4.

(4) Assay

50 μl of mitochondrial suspension from step (3) above is added to the 28 tubes from step (2) as follows: (at 15 second intervals):

| Tubes 1,2 | resuspension buffer (150 mM KCl, 5 mM Tris pH 7.4. |
|---|---|
| Tubes 3,4 | mitochondria from the isolation diluted 4:5 with resuspension buffer. |
| Tubes 5,6 | Incubation tube No. 1 |
| Tubes 7,8 | Incubation tube No. 2 |
| Tubes 9,10 | Incubation tube No. 3 |
| Tubes 11,12 | Incubation tube No. 4 |
| Tubes 13,14 | Incubation tube No. 5 |
| Tubes 15,16 | Incubation tube No. 6 |
| Tubes 17,18 | Incubation tube No. 7 |
| Tubes 19,20 | Incubation tube No. 8 |
| Tubes 21,22 | Incubation tube No. 9 |
| Tubes 23,24 | Incubation tube No. 10 |
| Tubes 25,26 | Incubation tube No. 11 |
| Tubes 27,28 | Incubation tube No. 12 |

The tubes are incubated for 5 minutes at 30° C. and then there is added to each tube, at 15-second intervals, 50 μl of concentrated HCl, 1.45 ml water and 1 ml of n-butanol. The tubes are mixed, chilled in ice for 20 minutes and then centrifuged for 10 minutes at 2500 rpm to clarify the layers. Thereafter, 500 μl of the upper butanol layer of each tube is pipetted into 100 μl of water and 500 μl butanol saturated water, the tubes are mixed and chilled in ice for 20 minutes and centrifuged again for 10 minutes at 2500 rpm. 200 μl of the butanol layer of each tube is pipetted into a scintillation vial to which is added 10 ml of Aquasol, and the samples are counted in a Packard Tri-Carb Scintillation Counter.

The results are used to calculated the percentage of inhibition of carnitine palmitoyl transferase by the compounds tested.

When tested in this assay, the compound of Example 2 (isomer A) and the prior art compound 2-[6-(4-chlorophenoxy)hexyl]oxirane-2-carboxylic acid ethyl ester (Compound A) gave the following results:

TABLE 1

| Compound Concentration, μM | Compound and % Inhibition ± SEM | | | |
|---|---|---|---|---|
| | Example 2 | | Compound A | |
| | liver | heart | liver | heart |
| 0 | 0 | 0 | 0 | 0 |
| 0.05 | 5 ± 3 | 6 ± 5 | 9 ± 7 | 5 ± 6 |
| 0.10 | 11 ± 5 | 17 ± 5 | 11 ± 6 | 8 ± 7 |
| 0.50 | 23 ± 7 | 18 ± 4 | 60 ± 7 | 36 ± 10 |
| 1.0 | 61 ± 9 | 34 ± 3 | 79 ± 2 | 38 ± 15 |
| 2.0 | 78 ± 7 | 35 ± 3 | 82 ± 2 | 51 ± 15 |
| 5.0 | 79 ± 8 | 40 ± 4 | 86 ± 3 | 68 ± 11 |
| 10.0 | 80 ± 9 | 50 ± 2 | 83 ± 3 | 81 ± 1 |
| 50.0 | 82 ± 10 | 52 ± 4 | 85 ± 2 | 84 ± 1 |
| IC$_{50}$ | .97 ± .18 | — | .33 ± .04 | .25 ± 1.5 |

The results show that while the two compounds tested demonstrate a significant inhibitory effect on liver carnitine palmitoyl transferase, the compound of the invention tested shows a very significantly reduced inhibitory effect on heart enzyme when compared to the prior art compound, evidencing a significantly lowered potential for adverse effect on normal heart function.

When tested in the above outlined procedure, two other compounds of the invention and the prior art compound 2-[6-(4-chlorophenoxy)hexyl]oxirane-2-carboxylic acid ethyl ester (Compound A) gave the following results:

| Compound of Example No. | Inhibition of Hepatic CPTase, IC$_{50}$, μM | % Maximal Inhibition of Cardiac CTPase at 50 μM |
|---|---|---|
| 7 (gem-difluoro compound | 0.35 | 26 ± 4 |
| 8 | 0.25 | 24 ± 6 |
| Compound A | 0.31 | 85 ± 2 |

These latter results show that not only do the compounds of the invention have a very significant effect on liver carnitine palmitoyl transferase but that the compounds also have an extremely reduced inhibitory effect on heart carnitine palmitoyl transferase when compared to the prior art compound, again evidencing a greatly lowered potential of adverse effect on normal cardiac function.

EXAMPLE 10

When tested in the above assay using liver mitochondria alone, other compounds of the invention give the following results.

TABLE 2

| Compound of Example No. | % Inhibition of Hepatic CPTase, IC$_{50}$, μM |
|---|---|
| 1 (isomer A) | 1.08 |
| 2 (isomer A) | 0.97 |
| 3 (isomer A) | 0.85 |
| 3 (isomer B) | 1.75 |
| 4 | 0.50 |
| 5 | 0.52 |
| 6 (gem-difluoro compound) | 5.9 |
| 6 (fluoro-vinyl compound) | 5.5 |
| 7 (fluoro-vinyl compound) | 0.70 |

The results show that the compounds tested exhibit significant carnitine palmitoyl transferase inhibition in liver mitochondria, evidencing excellent fatty acid oxidation inhibitory activity.

What is claimed is:

1. A compound having the formula

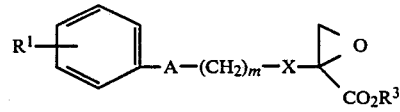

wherein

R$^1$ is hydrogen, hydroxy, lower alkyl, lower alkoxy, haloloweralkyl, halo or nitro;

R$^3$ is hydrogen, lower alkyl, or aryl of 7-12 carbon atoms;

X is —CH$_2$—CH—, —CH$_2$—C—  or —CH=C—;
         |            / \              |
         F           F   F             F

A is —CH$_2$—, —O— or —S—;

m is 1-8;

or a pharmacologically acceptable salt thereof.

2. A compound of claim 1 having the name 2-(1-fluoro-5-phenylpentyl)-2-oxiranecarboxylic acid methyl ester.

3. A compound of claim 1 having the name 2-[5-(4-chlorophenoxy)-1-fluoropentyl]-2-oxiranecarboxylic acid methyl ester.

4. A compound of claim 1 having the name 2-[6-(4-chlorophenxoy)-1-fluorohexyl]-2-oxiranecarboxylic acid methyl ester.

5. A compound of claim 1 having the name 2-[5-(4-chlorophenoxy)-1-fluoropentyl]-2-oxiranecarboxylic acid sodium salt.

6. A compound of claim 1 having the name 2-[6-(4-chlorophenoxy)-1-fluorohexyl]-2-oxiranecarboxylic acid sodium salt.

7. A compound of claim 1 having the name 2-[5-(4-chlorophenoxy)-1,1-difluoropentyl]-2-oxiranecarboxylic acid methyl ester.

8. A compound of claim 1 having the name 2-[5-(4-chlorophenoxy)-1-fluoro-1-pentenyl]-2-oxiranecarboxylic acid methyl ester.

9. A compound of claim 1 having the name 2-[6-(4-chlorophenoxy)-1,1-difluorohexyl]-2-oxiranecarboxylic acid methyl ester.

10. A compound of claim 1 having the name 2-[6-(4-chlorophenoxy)-1-fluoro-1-hexenyl]-2-oxiranecarboxylic acid methyl ester.

11. A compound of claim 1 having the name 2-[6-(4-chlorophenoxy)-1,1-difluorohexyl]-2-oxiranecarboxylic acid sodium salt.

* * * * *